United States Patent [19]

Woo

[11] 4,095,453
[45] Jun. 20, 1978

[54] DIFFERENTIAL THERMAL ANALYSIS CELL

[75] Inventor: Lecon Woo, Newark, Del.

[73] Assignee: E. I. Du Pont de Nemours and Company, Wilmington, Del.

[21] Appl. No.: 772,134

[22] Filed: Feb. 25, 1977

[51] Int. Cl.² ............................................ G01K 17/00
[52] U.S. Cl. .................................................. 73/15 B
[58] Field of Search ................ 73/15 B, 359; 136/230, 136/231

[56] References Cited

U.S. PATENT DOCUMENTS

| | | | |
|---|---|---|---|
| 3,285,053 | 11/1966 | Mazieres | 73/15 |
| 3,524,340 | 8/1970 | Kocherzhinsky et al. | 73/15 |
| 3,545,253 | 12/1970 | Iwata et al. | 73/15 |
| 3,554,002 | 1/1971 | Harden et al. | 73/15 |

FOREIGN PATENT DOCUMENTS 1,324,982  7/1973  United Kingdom .................... 73/15

*Primary Examiner*—Herbert Goldstein

[57] ABSTRACT

A heat flow type differential calorimeter uses a planar thermoelectric disc as its major heat flow path for transferring heat to the sample and reference capsules. To improve the reproducibility of the calorimeter, two small discs of a thermoelectric material capable of forming a thermocouple with the thermoelectric disc are attached thereto in face-to-face relationship. Next a thermocouple pair made of the same material as the small disc and a third material, capable of forming a thermocouple with the disc, is attached to the center of each of the small discs. This converts the usual point contact temperature sensor to a large surface area temperature sensor and hence improves the reproducibility of the thermal analyzer.

1 Claim, 4 Drawing Figures

DIFFERENTIAL THERMAL ANALYSIS CELL

BACKGROUND OF THE INVENTION

This invention relates to a differential thermal analyzer or calorimeter and, more particularly, to a differential thermal analyzer of a heat flow type using a thermoelectric disc to transfer heat to the sample.

There are many differential thermal analyzers available on the market today. Most of these analyzers utilize a heated block with sample and reference specimen capsules. The differential temperature changes that the sample undergoes relative to the reference material is used as an indication of the thermal properties of the sample under test.

One of the thermal analyzers presently available for effecting this test utilizes a thermoelectric disc made of constantan. The disc serves as a thermally conductive path for heat transfer to and from the sample. In addition, the disc serves as or provides a part of one of the differential temperature measuring thermocouples. Typically, the disc is firmly attached to a silver, programmed temperature surface and two symmetrically positioned, raised platforms serve as the sample and reference material holders. A chromel wire is connected to each platform to form a chromel-constantan differential temperature monitoring thermocouple. A purge gas is passed through the cell. An alumel wire is affixed also to the sample platform contiguous the chromel wire to provide a sample temperature sensing thermocouple. The outputs of the thermocouples are coupled to conventional amplifiers and eventually applied to an XY recorder wherein the differential temperature between the sample and the reference material is recorded on the Y axis and the temperature of the sample is recorded on the X axis.

While these thermal analyzers of the prior art are generally satisfactory, they suffer from the disadvantage of being sensitive to the placement or positioning of the sample material holder and the reference material holder (on the raised platform). Since the temperature of the sample and reference material is sensed from a point source, if the sample and reference holders or the thermocouple junctions are misplaced or mispositioned to any degree, the various runs are not reproducible and, in fact, not representative of the true thermal properties of the sample.

Accordingly, it is an object of this invention to obviate many of the disadvantages of these prior art thermal analyzers.

A further object of this invention is to provide an improved thermal analyzer that is capable of providing more reproducible results.

SUMMARY OF THE INVENTION

In accordance with this invention a cell for use in the differential thermal analysis of samples includes a thermally conductive disc at least a portion of which is fabricated of a first metal, the conductive disc having two face area regions each adapted to receive one of the sample material and reference material, a pair of second discs, each of a second metal capable of forming a thermocouple with the first metal and affixed to at least a portion of a different one of the face area regions of the conductive disc to form respective sandwich-like regions, a first lead of the second metal affixed to one of the second discs, a second lead of said second metal affixed to the other of the second discs, and a third lead of a third metal, capable of forming a thermocouple with the second metal, affixed to the one second disc and to the first lead at the point of contact with the one second disc. In a particularly preferred embodiment of this invention, the conductive disc is formed of constantan, the second disc of chromel and the third metal is alumel.

BRIEF DESCRIPTION OF THE DRAWINGS

Further advantages and features of this invention will become apparent upon consideration of the following description wherein.

DESCRIPTION OF THE PREFERRED EMBODIMENT

Figure 1:
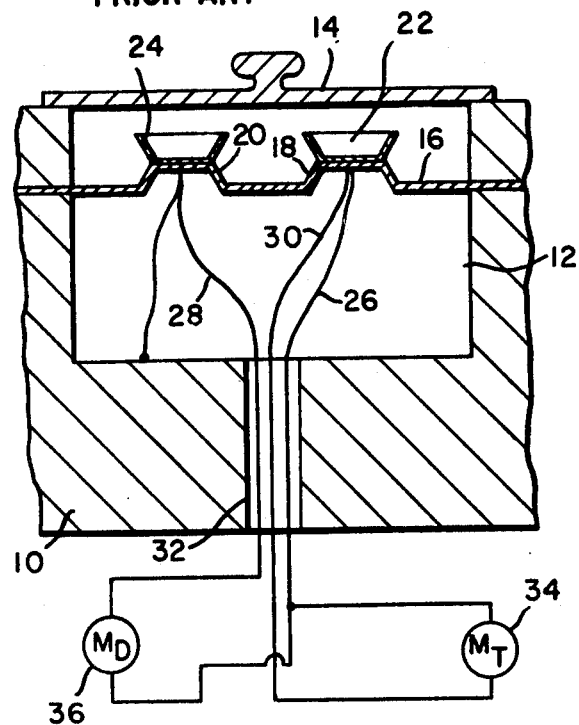
FIG. 1 is a fragmentary cross-sectional elevation view of a portion of a differential thermal analysis cell constructed in accordance with the prior art.

The differential thermal analysis cell of the prior art depicted in FIG. 1 includes a heating block 10 (typically a metal block surrounded by a suitable heating element electric or otherwise-not shown). The heating block 10 defines a sample chamber 12, open at the top portion thereof and adapted to be closed by a suitable lid 14. Across the midportion of the sample chamber 12 is disposed a thermoelectric disc 16 having a raised sample platform 18 and reference platform 20. These platforms support, respectively, a disposable sample capsule, holder, or cup 22 and a reference capsule, holder, or pan 24 of known type. The thermoelectric discs are made of any suitable thermocouple forming material, preferably one having a high response to temperature such as constantan. Any of the other known suitable thermoelectric or thermocouple forming materials such as chromel, alumel, etc., also are used.

Leads or wires 26, 28 of a different metal than the disc 16, such as chromel, which different metal is capable of forming a thermocouple junction with the metal of the thermoelectric disc, are attached (using known techniques) to the midportion of each of the respective platforms 18 and 20, thus forming a chromel-constantan differential temperature monitoring thermocouple. Another lead wire 30 of a still different metal, such as alumel, from either of the disc 16 or lead wires 26, 28, and capable of forming a thermocouple junction with the lead wire 26, is attached to the same point on the sample platform 18 as the lead wire 26. This provides a temperature sensing thermocouple 26-30 for the sample platform.

These lead wires 26, 28 and 30 are coupled through an axial bore 32 formed in the block 10 and to suitable measuring circuits depicted by the meters 34 and 36. The meter 34 is designed $M_t$ for sample temperature, and the meter 36 is designated $M_d$ for measuring the differential temperature between the reference and sample. These meters 34 and 36 may be assumed to include the amplification necessary to provide a suitable output to a conventional XY recorder of known type (not specifically shown but assumed to be included in the meters). In this manner, a plot may be obtained of the differential temperature along the Y axis as a function of the temperature within the sample chamber along the X axis.

The use of the thermoelectric disc 16 serves to provide a fixed and reproducible path of heat transfer and one in which the thermal resistance can be adjusted to yield optimum sensitivity and resolution by adjusting the size and thickness of the disc. The particular thermocouple pair, i.e., chromel-constantan for differential temperature sensing, is used because of its favorable output signal versus temperature profile. The sample holders or cups 22, 24 typically are small aluminum cups which may be disposed of after use.

Figure 2:
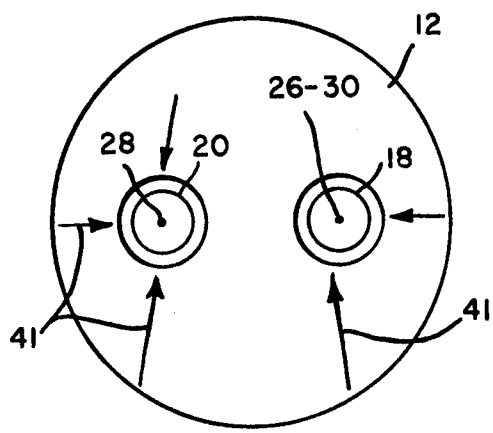
FIG. 2 is a diagrammatic plan view of the thermally conductive disc employed in the cell depicted in FIG. 1 illustrating heat flows to the temperature sensing regions.

Although particularly useful, this cell just described can have some disadvantages for the reasons particularly shown in FIG. 2. In FIG. 2 there is seen the two platforms 22 and 24 with the dots 28 and 26–30 depicting the thermocouple junctions associated with each particular platform. Heat is transferred into the sample chamber 12 from the periphery of the disc along the path depicted by the arrows 41. It is readily apparent from this diagram that if the sample holders 22 or 24 are misplaced at all relative to the platform 18 or 20 they will receive a greater or lesser heat transfer than desired. In addition, if the sample holders 22 or 24 are uneven on their bottoms such that they do not have a uniform contact with the platforms 18 and 20, their temperature may be improperly sensed or at least sensed differently on different runs, and they are apt to receive unequal and non-uniform amounts of heat. Hence, there are problems in reproducbility and reliability incumbent with such point contact temperature sensing. Also, the thermocouple junctions must be accurately placed in the center of the platforms.

Figure 3:
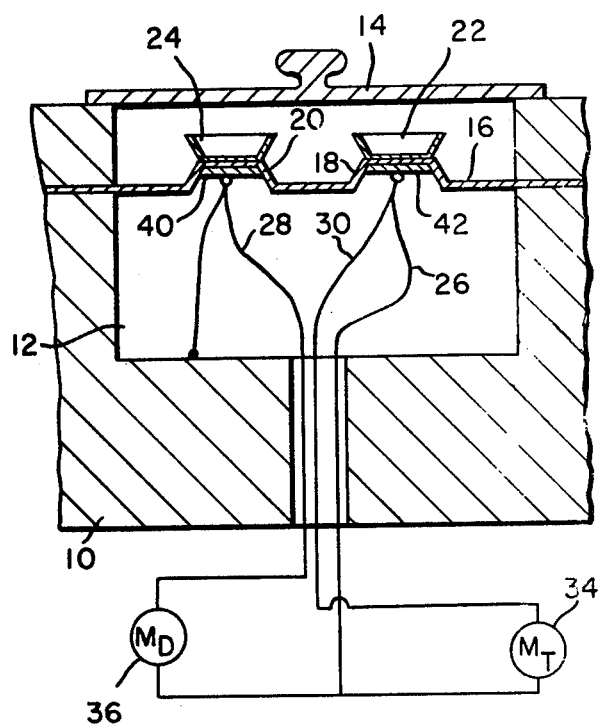
FIG. 3 is a fragmentary cross-sectional elevation view of a differential thermal analysis cell constructed in accordance with this invention.
Figure 4:
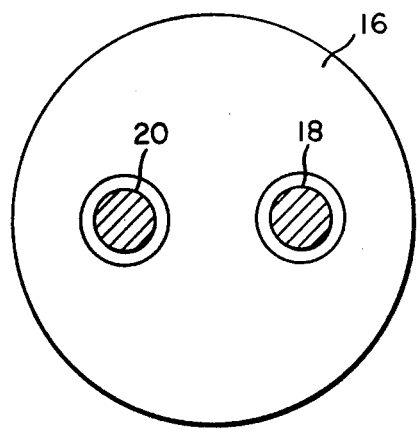
FIG. 4 is a plan view of a thermoelectric disc employed in the cell depicted in FIG. 3.

In accordance with this invention, the cell depicted in FIG. 1 is improved, as depicted in FIG. 3, by affixing discs 40 and 42 to the underside of corresponding ones of the respective platforms 18 and 20. These discs 40 and 42 are made of the same thermoelectric metal as the lead wires 26 and 28, i.e., any metal that is capable of forming a thermocouple junction with the thermoelectric disc 16. Affixing may be accomplished in a conventional manner, such as spot welding, cladding, and the like so long as a constant and uniform thermocouple contact or junction is formed over the adjoining face or surface areas of the discs 40 and 42 on the one hand and the underside of the platforms 18 and 20 on the other hand, thus to form respective sandwich-like wide area thermocouples. Following this, the leads 26 and 28 are connected to the underside of the respective discs 40 and 42 in the same manner as they were previously connected to the underside of the platforms 18 and 20. The lead or wire 30 is connected to the underside of the disc 40 in the same manner as it previously was connected to the underside of the platform 20. The lead wire 30 may be any suitable material capable of forming a thermocouple with the lead 26. This has the unique advantage of expanding the surface area of the differential temperature thermocouples so as to encompass a much greater surface area as that depicted by the shaded area 44 in FIG. 4. The entire surface area of the platforms 18 and 20 is shaded to depict that they are now the total sensing area.

With this configuration, even if the sample holders 22 and 24 do not make constant or uniform contact at any portion of the surface, due to the averaging effects of the total surface area, reproducibility is assured. In effect, this new junction constitutes a multiple thermocouple array where the thermocouples' voltages are summed in parallel. The integrating and averaging effects of this area sensing scheme reduces positional errors significantly. Since the sample and reference materials are sensed over a larger surface area, the precision placement requirements of the point-type thermocouple are avoided. This facilitates an easier, cheaper construction.

In a typical cell that has been constructed, the thermoelectric disc 16 is 3.5 cm in diameter, 0.12 mm thick, and is formed of constantan. The discs 40, 42 are 0.5 cm in diameter, of the same thickness as the disc 16, and formed of chromel. The remaining leads are alumel. Such cell is relatively easily constructed and is relatively free of inaccuracies due to sample holder positional errors.

An alternative form of construction fabricates the outer portion of the disc 16 of any suitable ceramic for conducting heat. The inner portion has swaged therein a pair of smal thermoelectric discs which provide the actual platforms 18 and 20 (FIG. 3). Otherwise, the remaining construction and function is identical to that described in conjunction with FIG. 3. The advantage of the ceramic usage is that it permits higher temperature operation. Alternatively, the platforms may be inverted and cup-like or they may be totally planar.

I claim:

1. A cell for use in the differential thermal analysis of sample materials comprising:

a thermally conductive disc at least a portion of which is fabricated of a first metal, said metal portion of said conductive disc having two face area regions each adapted to receive one of said sample materials and a reference material, said conductive disc having an outer portion fabricated of a ceramic and an inner portion fabricated of said first metal;

a pair of second discs each disc having a face, being fabricated of a second metal capable of forming a thermocouple with said first metal, and affixed to at least a portion of a different one of said face area regions of said conductive disc in face-to-face relationship to form respective sandwich-like thermocouple regions for said sample and reference materials;

a first lead of said second metal affixed to one of said second discs;

a second lead of said second metal affixed to the other of said second discs; and means for sensing the temperature of said sample material.

* * * * *